United States Patent [19]
Kunze, Jr. et al.

[11] Patent Number: 6,134,968
[45] Date of Patent: Oct. 24, 2000

[54] PORTABLE ACOUSTIC IMPEDANCE MEASUREMENT SYSTEM

[75] Inventors: Robert K. Kunze, Jr., Derby; Mary K. Drouin; Judith M. Gallman, both of Wichita, all of Kans.

[73] Assignee: The Boeing Company, Seattle, Wash.

[21] Appl. No.: 09/356,058

[22] Filed: Jul. 19, 1999

[51] Int. Cl.$^7$ .................................................. G01N 29/00
[52] U.S. Cl. ................................................................ 73/589
[58] Field of Search ..................................... 73/589, 584

[56] References Cited

U.S. PATENT DOCUMENTS

| | | |
|---|---|---|
| 2,837,914 | 6/1958 | Caldwell .................................. 73/589 |
| 2,981,096 | 4/1961 | Carrell . |
| 3,294,193 | 12/1966 | Zwislocki ................................. 73/589 |
| 3,883,841 | 5/1975 | Norel et al. .............................. 73/589 |
| 3,915,016 | 10/1975 | Jhaveri et al. . |
| 3,960,004 | 6/1976 | Wirt et al. ................................ 73/589 |
| 4,302,295 | 11/1981 | Shimada . |
| 4,305,295 | 12/1981 | Andersson et al. . |
| 4,445,378 | 5/1984 | Zuckerwar . |
| 4,522,283 | 6/1985 | Smith . |
| 4,537,630 | 8/1985 | Syed . |
| 4,644,794 | 2/1987 | Vaicaitis . |
| 4,648,275 | 3/1987 | Goodman . |
| 4,651,566 | 3/1987 | Andersson et al. . |
| 4,732,039 | 3/1988 | Syed . |
| 4,763,524 | 8/1988 | Goodman . |
| 4,768,379 | 9/1988 | Arcas et al. . |
| 5,377,546 | 1/1995 | Arcas et al. . |
| 5,684,251 | 11/1997 | Arcas et al. . |
| 5,712,805 | 1/1998 | Wang et al. . |

*Primary Examiner*—Richard A. Moller
*Attorney, Agent, or Firm*—Christensen O'Connor Johnson Kindness PLLC

[57] ABSTRACT

A portable acoustic impedance data acquisition and processing system is provided for use with a test object. The system includes a dynamic signal analyzer, a test head, a removable microphone holder, a cylindrical endcap fitting, an amplifier, and one or more power supply sources. The test head includes a compression driver and a cylindrical waveguide tube. The waveguide tube has a first end connected to the compression driver and a second end that is open. The removable microphone holder is attachable to the waveguide tube near its second end and a number of microphones are insertable into the microphone holder. During use, the dynamic signal analyzer provides audio output test signals that are amplified by the amplifier and fed to the compression driver for use as the acoustic test signal. The microphones provide measured signals to the dynamic signal analyzer which analyzes them and makes the results available to the operator. The endcap fitting is for use in calibrating and adjusting microphone measurements prior to actual testing. The fitting includes a first end adapted to engage the second end of the waveguide tube and a second end having a mounting disc into which the microphones may be held longitudinally.

9 Claims, 7 Drawing Sheets

PORTABLE ACOUSTIC IMPEDANCE MEASUREMENT SYSTEM

FIELD OF THE INVENTION

The present invention relates to acoustic impedance data acquisition and analysis systems, and more particularly, to portable two-microphone systems for on-site data analysis.

BACKGROUND OF THE INVENTION

Acoustic liners are designed to suppress noise generated at particular frequencies. A typical single degree of freedom liner includes a sheet of honeycomb core with a solid backface and one or more porous facesheets. Some liner configurations include multiple core layers and various additional bulk absorbers. Acoustic impedance is composed of two parts, resistance and reactance. The acoustic impedance characteristics of a liner can be used as an assessment of the noise attenuation properties of the liner.

In the aircraft industry, acoustic liners are commonly used to attenuate noise in aircraft engines, in machinery used in aircraft production and maintenance facilities, and at airport buildings. In many aerospace applications, it is necessary to test an acoustic liner after it is installed at a permanent location, and to continue testing and monitoring the liner at different points in time. This ensures that the liner continues to operate as expected and continues to meet regulatory noise emission standards. Such on-site testing requires a portable acoustic testing device to be taken to the installation site and used on the liner to check for the acoustic output of the part, or in some instances, of an entire assembly having one or more acoustic liner components.

U.S. Pat. No. 5,684,251 describes a portable acoustic testing device that uses a digital audio tape player, an amplifier, a test head, an audio recorder, a battery power supply, and a spectral analyzer. The tape player provides an output test signal which is amplified and sent to the test head. The test head includes an acoustic signal generator and a waveguide that is positionable adjacent the liner being tested. The test head uses the test signal to elicit an acoustic response from the liner. A number of pressure transducers, or microphones, measure the liner response and send the information to the recorder for storage. The recorder then provides the information to the spectral analyzer which performs the desired acoustic analyses on the recorded acoustic response data signals.

The '251 device has a number of drawbacks. One disadvantage is that it is cumbersome to use due to the need to record the response data signals and then feed them into the signal analyzer for analysis. Another problem is that the microphones are frequently uncalibrated and are effected differently by variations in the system. This can cause errors in the final test results. Another disadvantage is that the test head used in the '251 device does not work well with all shapes and sizes of liners. In particular, for flat liner surfaces, the cupped end of the test head can be a hindrance to properly fitting the test head against the liner during, testing. In addition, the '251 device does not appear to be capable of testing small liner sections, such as noninstalled liner plug samples that are smaller in size than the '251 test head output end. Lastly, the '251 device does not appear to adequately protect a worker from accidental exposure to excessive noise levels during use. The '251 device has two switches that must be pressed in order to activate the '251 device. Although this is helpful, it does not ensure that the test head itself is properly positioned, i.e., the switches may be accidentally pressed when the test head is not positioned adjacent a liner.

Thus, a need exists for an improved portable acoustic measurement system. The ideal system would directly analyze test result signals and would ensure that both microphones are properly calibrated so that the affect of system components on the measured data are accounted for. In addition, the system would benefit from having a test head that could be easily used on all sizes and shapes of acoustic materials, including non-installed test plug samples. Further, the ideal system would provide additional noise safety features to avoid any inadvertent sounding of the test head. The present invention is directed to fulfilling these and other needs as described below.

SUMMARY OF THE INVENTION

According to teachings of the present invention, a portable acoustic impedance data acquisition and processing system is provided for use with a test object. The system includes a dynamic signal analyzer, a test head, two microphones, an amplifier and one or more power supply sources. The test head includes a compression driver for providing an acoustic signal and a cylindrical waveguide tube. The waveguide tube includes a first end connected to the compression driver and a second end that is open. The tube also includes a side opening.

A removable microphone holder is attached to the waveguide tube at its side opening. The microphones are insertable into the microphone holder. During use, the dynamic signal analyzer creates audio output test signals that are amplified by the amplifier and fed to the test head where they are then applied to the test object. The microphones measure the results of the applied signal and provide the measurements back to the dynamic signal analyzer where they are analyzed and made available to the operator.

The arrangement further includes a cylindrical endcap fitting, a mounting disc, and a plug for use in calibrating and adjusting microphone measurements. The endcap fitting includes a first end adapted to engage the second end of the waveguide tube and a second end having an opening to hold the mounting disc. The mounting disc holds the microphones at a longitudinal orientation during calibration. The plug is positioned within the waveguide tube side opening during calibration to prevent the loss of a test signal.

In accordance with aspects of this invention, various types of interface members are provided for use with different types of test objects. The interface member attaches to the second end of the waveguide tube to facilitate positioning of the test head against a test object. In one embodiment, the member is a flexible annular interface gasket for use with flat or slightly curved test object surfaces. In another embodiment, the interface member is a rigid flat annular adapter attached to the wave guide tube second end and a flat compressible annular gasket that is held in place by a groove cut into the face of the adapter. In yet another embodiment, the interface member is a plug sample holder for use with small test samples.

In accordance with further aspects of this invention, a safety system is provided to ensure use of an amplified signal only when the test head is appropriately placed on a test object. The safety system includes a harness attached to the second end of the waveguide tube. The harness has at least two arms extending radially therefrom. Each arm has a switch having a compressed state and an extended state. The switches are electrically linked in series and are connected to the amplifier and adapted to disrupt the amplifier from providing an amplified signal when any one of the switches is in an extended state.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figures 1, 3:
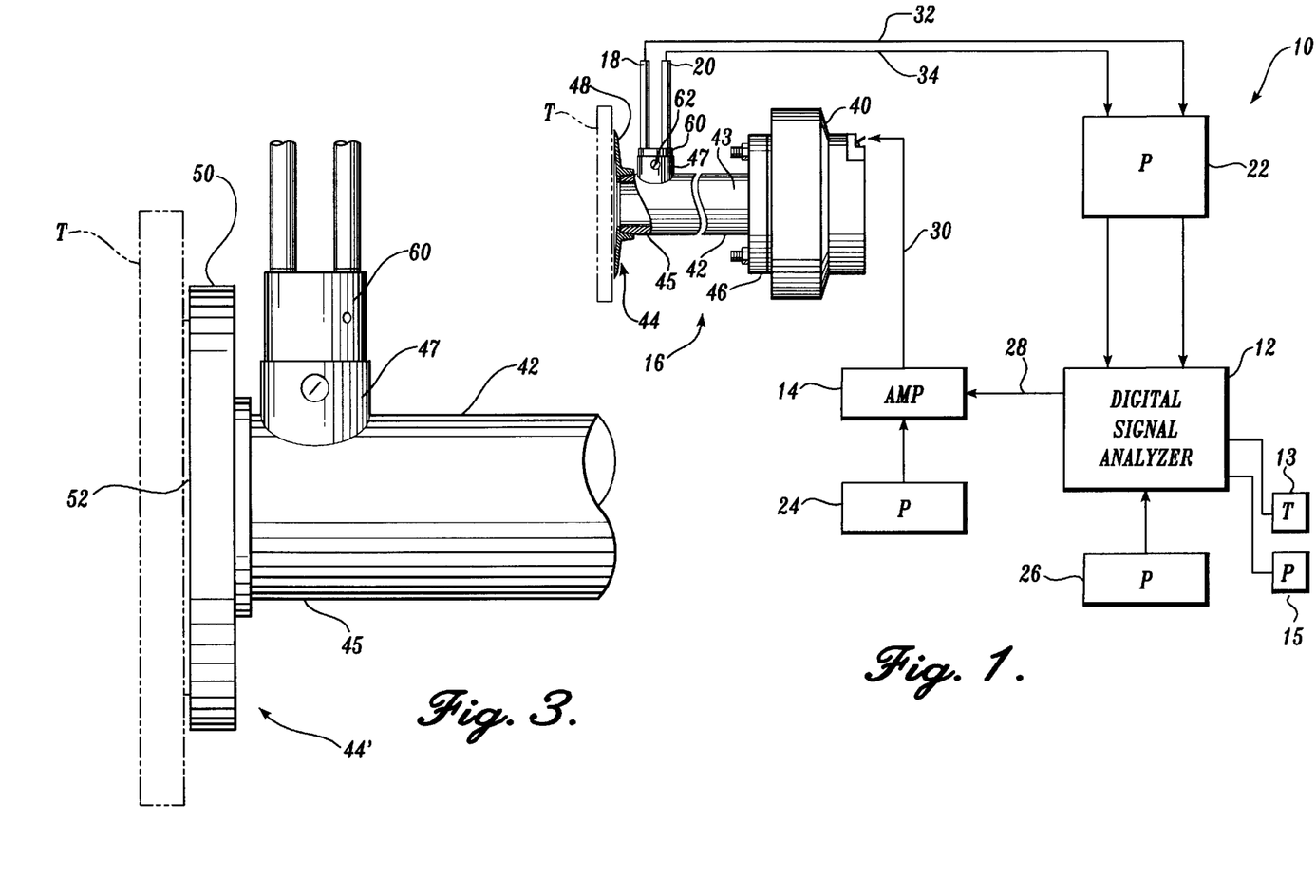
FIG. 1 is a schematic block diagram illustrating a portable acoustic impedance measurement system formed in accordance with the present invention.
FIG. 3 is a side view of an alternative interface member formed in accordance with the present invention.

The present invention is a portable acoustic measurement system for use with an acoustic test object T, such as an engine liner, a nacelle assembly, an acoustic wall panel, a liner plug sample, etc. Referring to FIG. 1, the present invention portable acoustic measurement system 10 includes a dynamic signal analyzer 12, an amplifier 14, a test head 16, two microphones 18, 20 attached to the test head, and various power supplies 22, 24, 26. In general, the dynamic signal analyzer 12 provides an audio test signal to the amplifier 14 via a cable 28. The amplifier 14 amplifies the test signal and provides it to the test head 16 via cable 30. The test head 16 applies the amplified signal to the test object T. During this application, the microphones 18, 20 sense the test object response and provide output results via lines 32, 34 to a microphone power supply 22. The microphone power supply 22 provides modulated power to the microphones and is capable of amplifying the output signal. The microphone power supply 22 forwards the resulting output signal (gains can be applied as necessary) to the dynamic signal analyzer 12 for analysis and reporting.

In more detail, the dynamic signal analyzer (DSA) includes a conventional dynamic signal spectrum analyzer, such as Hewlett Packard model HP35670A, coupled to optional input/output devices (e.g., a keyboard, printer, modem, etc.) The DSA performs a number of different functions. It generates an audio test signal, acquires measured data from the microphones 18, 20, performs an acoustical analysis of the measured data, and prepares a report of the results to the operator via a display or via an electronic storage medium, such as a floppy disk. In one embodiment, the DSA also connects to temperature and pressure sensors, 13 and 15, respectively, so that these factors may be accounted for in the DSA analysis.

The DSA audio test signal is preferably in the range of about 0 to 5 volts RMS (root mean square) in the form of a random noise signal, a fixed sine signal, or a swept sine signal. The majority of the testing for aircraft acoustic test objects is preferably conducted using only random noise audio test signals. Multiple sound pressure levels are measured for each location when the broad band/random noise signal is used. These measurements are taken automatically whenever a location is tested and the values of the sound pressure levels and the number of levels may be modified as necessary.

The amplifier 14 power amplifies and filters the DSA's audio test signal in order to provide the test head 16 with an audio signal of sufficient power to generate sound pressure levels ranging from about 115 dB to about 150 dB. The amplified and filtered signal is preferably stable within the range of about 20 Hz to about 10,000 Hz, and particularly in the frequency range of about 700 Hz to about 6000 Hz when used in aerospace applications. This range contains the frequencies of greatest concern when simulating engine noise, as well as eliminates frequencies that are too high or too low for accurate resolution given the physical dimensions of the measurement system, as described below.

Still referring to FIG. 1, the test head 16 includes a compression driver 40, a waveguide tube 42, and an interface member 44. The compression driver may be a conventional driver, such as an Altec Lansing model 909-8A compression driver or other loudspeaker. The compression driver has a throat diameter of about 1 inch or less. It is preferable to use a compression driver having an easily replaceable diaphragm.

The waveguide tube 42 is a cylindrical tube with first and second ends 43, 45, and a cylindrical inner chamber of approximately 1.2 inch (3.0 cm) diameter. The first end 43 is secured to the compression driver 42 using an annular mounting plate 46 bolted therebetween. Changing compression drivers is thus a relatively straightforward procedure of unbolting the mounting plate 46 from the compression driver 40 and rebolting the mounting plate to another compression driver. The waveguide tube second end 45 is open and positionable near the test object T during use. Upon receiving an amplified audio test signal from the amplifier 14, the compression driver 40 generates a sound wave that is transmitted down the waveguide tube 42 to the test object T. The waveguide tube 42 includes an upper fitting 47 through which a microphone holder 60 is held.

Figure 2:
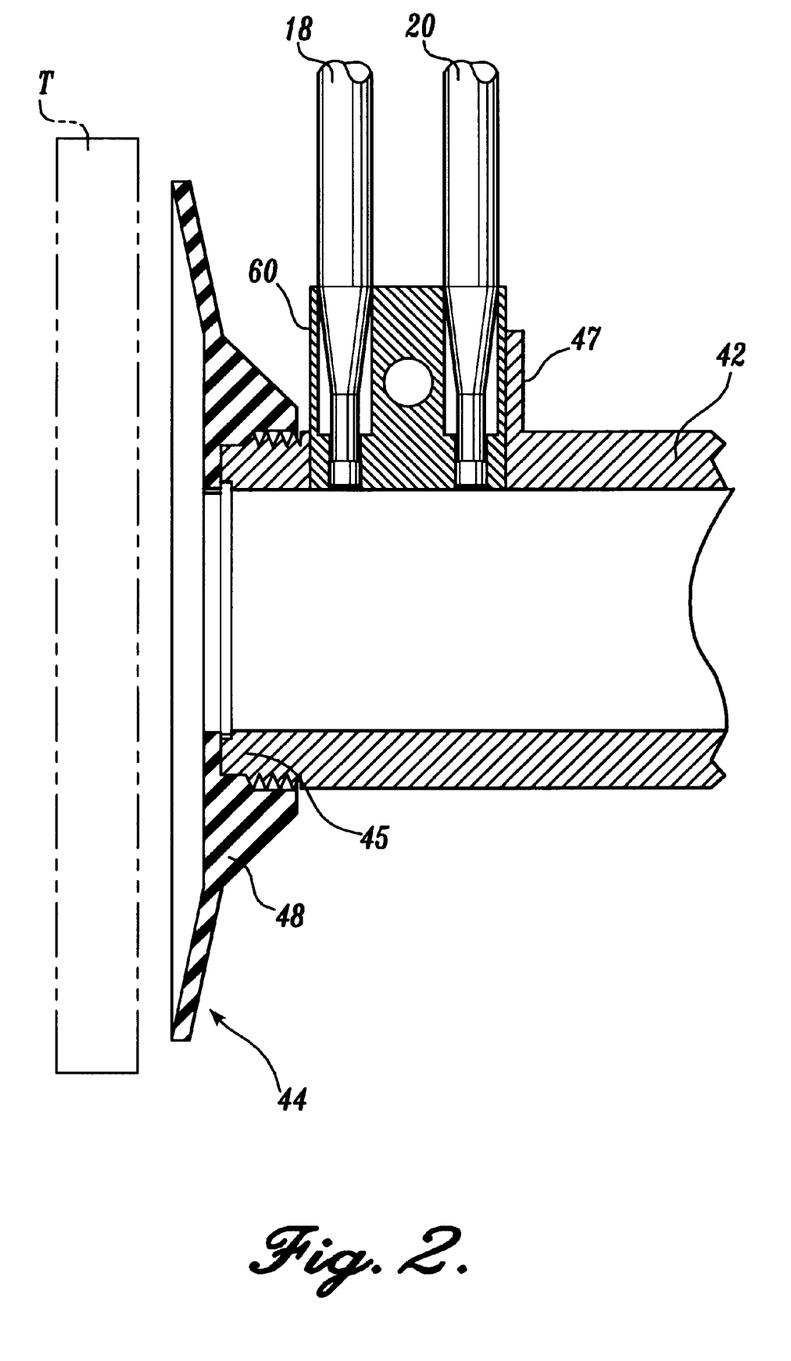
FIG. 2 is a cross-sectional side view of the interface member shown in FIG. 1.

The interface member 44 is removably attached to the second end 45 of the waveguide tube to ensure proper placement between the test head 16 and the test object T. Various forms of interface members are provided herein and should be used according to the particular size and shape of test object T of a given application. As will be appreciated by those skilled in the art upon reading this, various other embodiments may come to mind and are to be considered within the scope of the present invention. FIGS. 1 and 2 illustrate a first embodiment of an interface member for use with flat or slightly curved test objects. The interface member 44 is formed as a flexible annular gasket 48 having a slight outwardly-cupped shape. In one embodiment, the gasket has an inner diameter of about 3 cm and an outer diameter of about 10.5 cm. During use, the gasket 48 forms a seal around the test object to inhibit test sounds from exiting outwardly from the waveguide second end or through the facesheet adjacent to the test location. The flexible annular gasket 48 conforms to the shape of the second end 45 of the waveguide tube 42 and has an inner diameter that is slightly smaller than the outer diameter of the waveguide tube 42 so that it is held in position by compressional forces.

Figure 4:
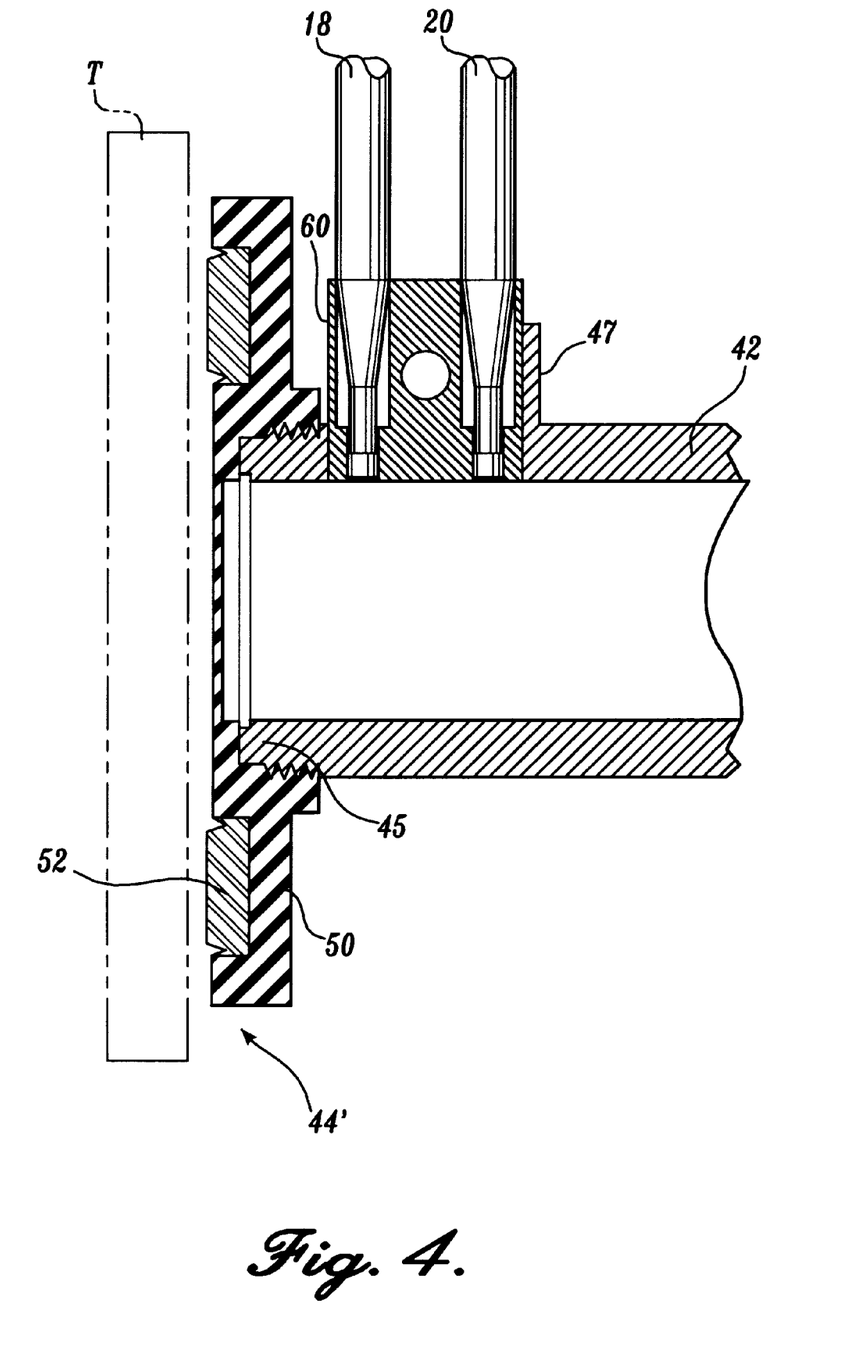
FIG. 4 is a cross-sectional side view of the member of FIG. 3.

FIGS. 3 and 4 illustrate a second embodiment of an interface member for use with flat, rigid test objects. The member 44' includes a flat rigid annular adapter 50 with a compressible annular ring 52 held in a groove in the outward face of the adapter 50. Unlike the flexible gasket, the annular adapter 50 is threaded and screws onto mating threads formed in the exterior surface of the second end 45 of the waveguide tube 42.

Figure 7:
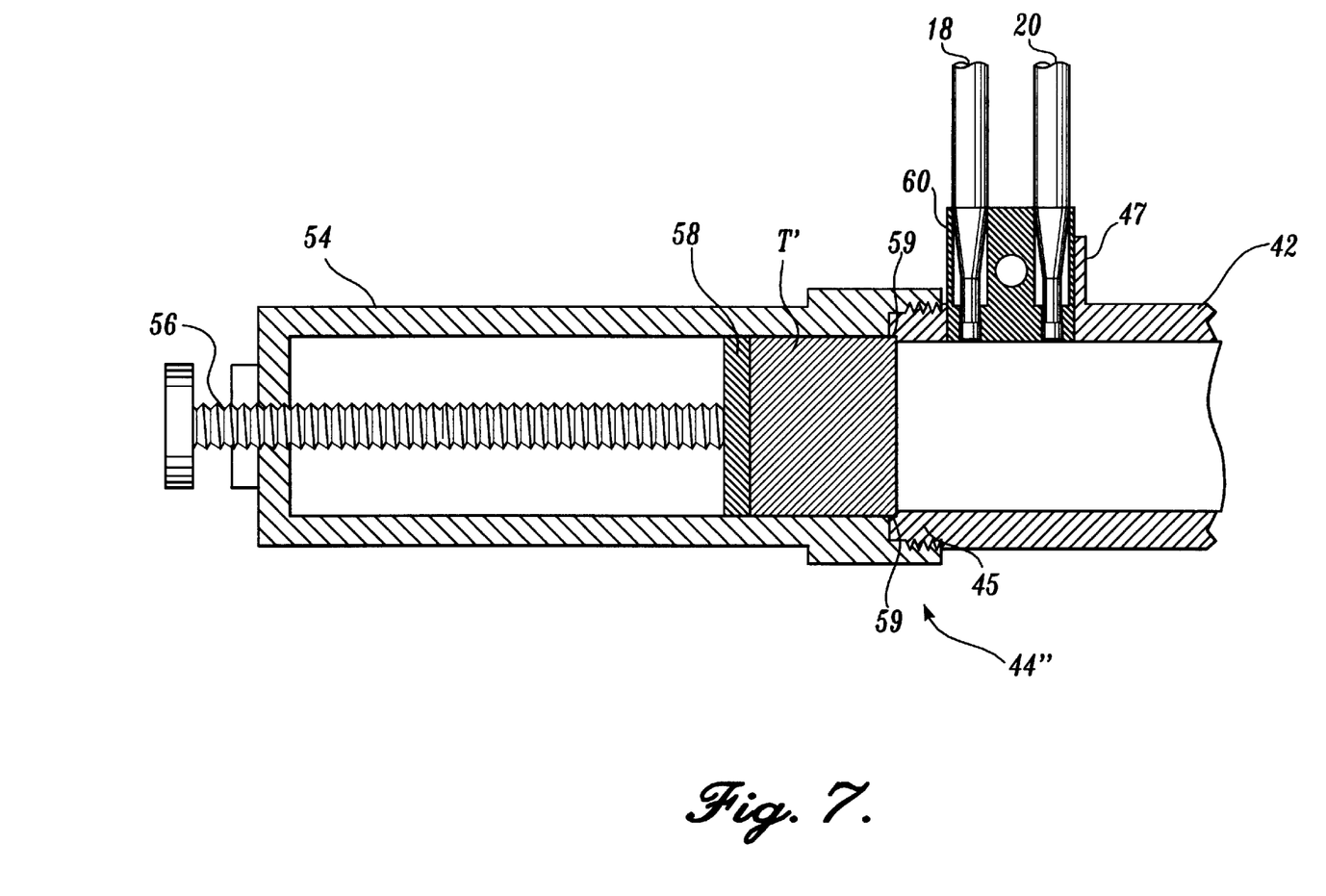
FIG. 7 is a side view of a plug-sample interface member formed in accordance with the present invention.

FIG. 7 illustrates a third embodiment of an interface member 44" for use with a plug sample test object T'. The member includes a cylindrical tube 54 having a rod 56 threaded through a hole in the tube distal end. The rod 56 is oriented along the longitudinal axis of the tube 54. Within the tube 54, the rod 56 is attached to a push plate 58. A tube proximal end is attached to the waveguide tube second end 45 in a manner similar to the attachment used with the flat rigid annular adapter described above. During use, the plug sample test object T' is held within the cylindrical tube 54 by action of the rod causing the push plate to push the test sample T' toward the waveguide tube second end 45. A lip 59 is available within waveguide tube 42, to maintain the test object T' at a desired location at the waveguide tube second end opening.

Referring back to FIG. 1, the microphone holder 60 is connected to the waveguide tube second end via a removable pin 62 or other fastening element. Various types of microphone holders may be used, to permit the use of different sizes and brands of microphones (or pressure transducers of some type). The microphones 18, 20 are held within the microphone holder 60 at an orientation transverse to the longitudinal axis of the waveguide tube 42, though at unequal longitudinal distances from the waveguide tube second end. The waveguide tube 42 includes an opening at the location of the microphone holder 60. The microphone holder matches the shape of the inner diameter of the waveguide tube 42 so that the microphones 18, 20 are flush or very slightly recessed with respect to the waveguide tube cylindrical inner chamber. In preferred embodiments, microphone 18 is positioned approximately 1.544 cm (0.608 inches) from the test object T, and microphone 20 is positioned approximately 3.068 cm (1.208 inches) from the test object T. The microphones provide measured signals to the dynamic signal analyzer 12 via the microphone power supply 22.

To improve the accuracy of the DSA analysis, the microphones are calibrated prior to running tests on a test object T. The microphones are calibrated using a known source (a particular frequency at a known sound pressure level); however, simply calibrating the microphones to a known signal may not be sufficient to ensure that the data acquired is not affected by other components in the systems. Because measurements may be affected by differences in the microphone sensitivities, possible power supply bank differences, data acquisition channel peculiarities, and other influences, any analysis done should preferably take into account these influences and adjust for them as well.

In one embodiment of the present invention, measurements are done by conducting a first test with a known source and then reversing the microphones in location and conducting a second test using the same known source. For both tests, the frequency response function of the measured results is recorded. The reversed frequency response function is "averaged" with the frequency response function in the forward direction. The averaged frequency response function is used in the calculation of the test sample impedance. This averaging of the frequency response functions eliminates errors in the data caused by the differences between the microphones.

Figure 5:
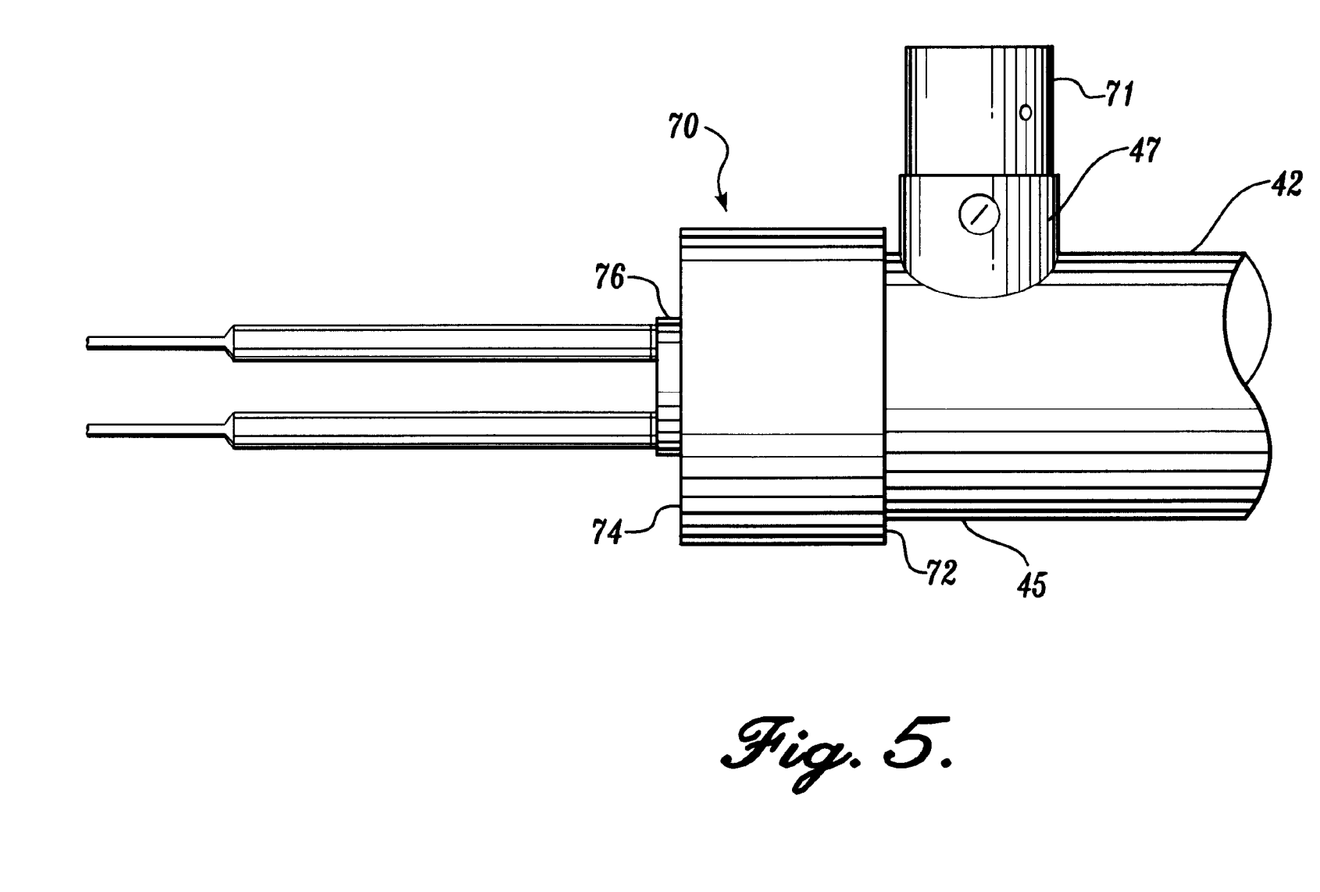
FIG. 5 is a side view of a calibration interface member formed in accordance with the present invention.
Figure 6:
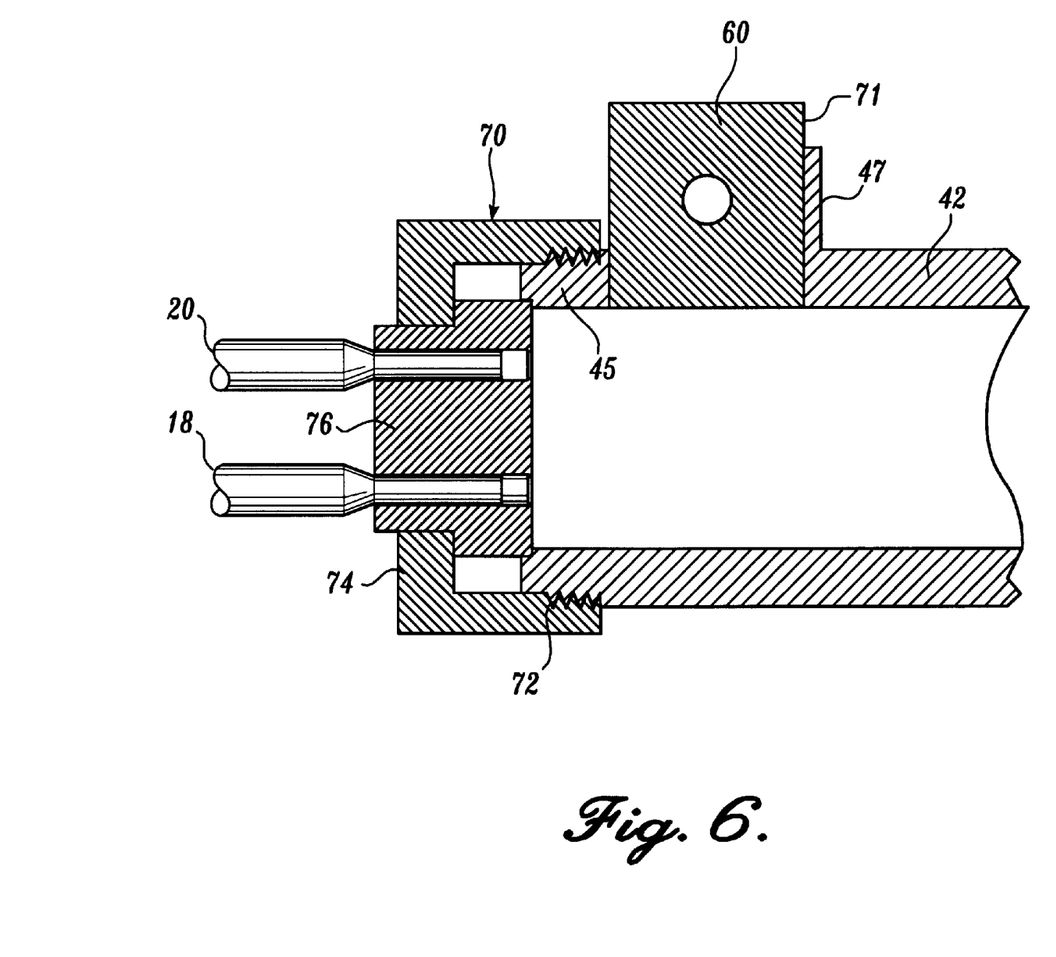
FIG. 6 is a cross-sectional side view of the member of FIG. 5.

Referring to FIGS. 5 and 6, in another embodiment of the present invention, an endcap fitting 70 is provided for use in calibrating the microphones. The endcap fitting is a cylindrical member having one end 72 connectable to the second end 45 of the waveguide tube 42. The other end 74 of the endcap 70 holds a mounting disc 76 into which the microphones are inserted and held during calibration measurements. A solid plug 71 is insertable into the microphone holder 47 to prevent the test signal from escaping the waveguide tube 42 and resulting in an invalid calibration measurement.

As shown best in FIG. 6, the microphones 18, 20 are oriented directly at the output of the waveguide tube (i.e., parallel to the longitudinal centerline of the waveguide tube and of equal distance to the waveguide tube second end 45). In this position, both microphones are simultaneously subjected to the same acoustic pressure. Any differences between the microphone measurements are recorded by the DSA in the frequency response function. These frequency response functions represent corrections (normalizations) that should be applied in the analysis of the microphone measurements that are taken when the microphones are in their normal position in the waveguide tube. The use of these corrections helps to ensure accurate test results. The endcap fitting information is stored in the DSA or on a computer disk for each microphone pair.

Power is provided to the system via one or more conventional power supply sources. In the embodiment of FIG. 1, three separate power supplies are shown—a battery power supply 22 for the microphones, an outlet power supply 26 for the analyzer 12, and a battery power supply 24 for the amplifier. Alternatively, these supplies may be provided from a single source, as circumstances warrant.

Because the portable impedance system is capable of producing extremely high sound pressure levels (SPLs) within the waveguide, preferred embodiments of the present invention include a safety system 80 to prevent accidental emission of extreme SPLs. Federal regulations prohibit any exposure to SPLs above a certain level (currently 115 dB) and limit exposure at that level to a maximum time amount (currently 15 minutes time weighted average for an 8 hour work day). The normal operating range of an impedance measurement system in the aerospace industry is in the range of about 115 dB to about 150 dB, with a majority of testing conducted at SPLs at or above 135 dB.

Figure 8:
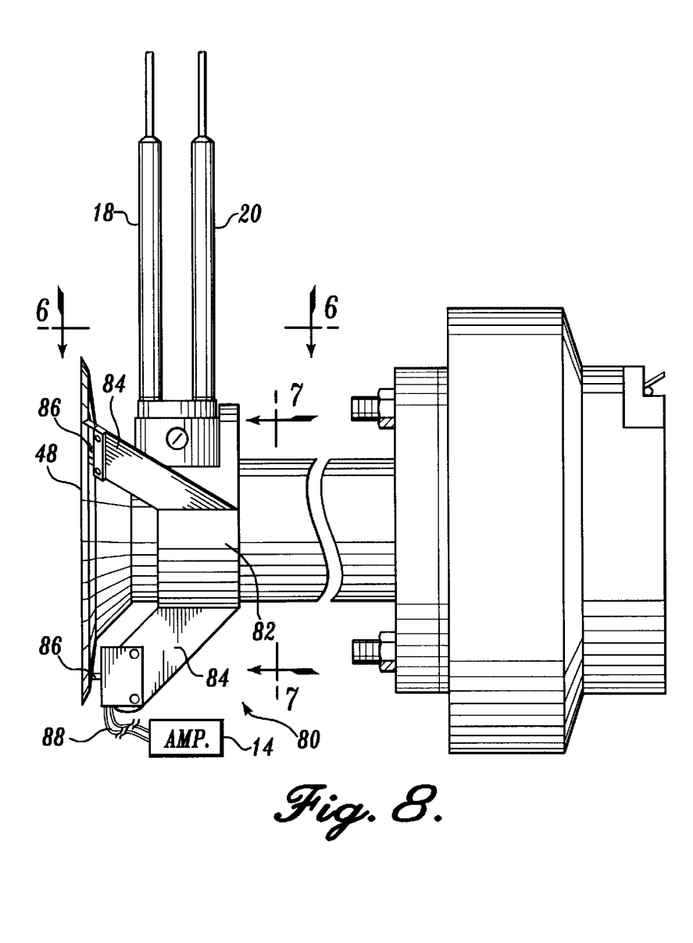
FIG. 8 is a side view of a safety system formed in accordance with the present invention.
Figure 9:
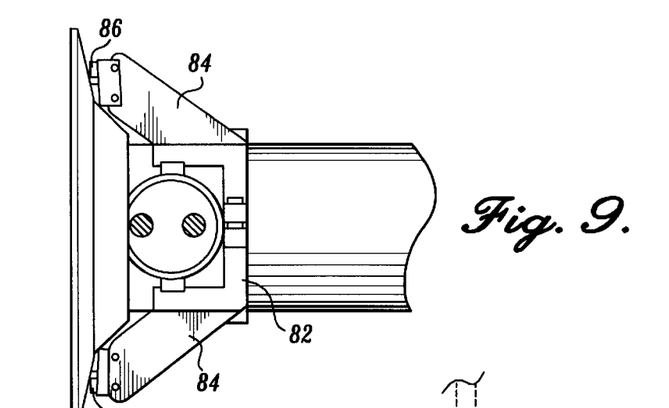
FIG. 9 is a top down view taken along line 6—6 in FIG. 8.
Figure 10:
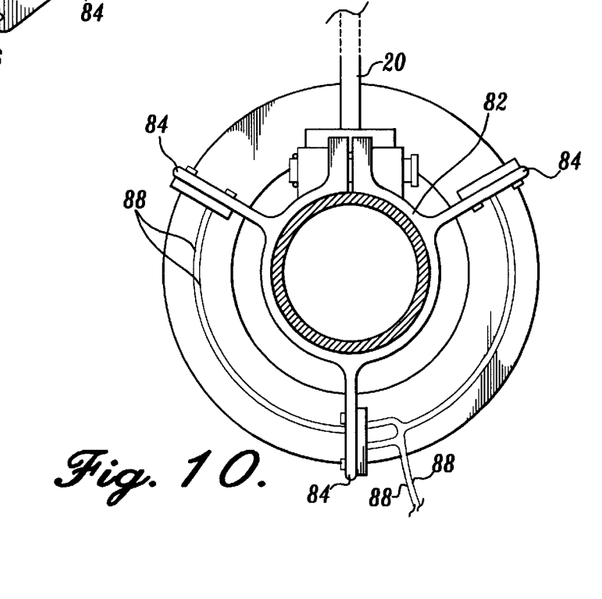
FIG. 10 is a cross-sectional view taken alone line 7—7 in FIG. 8.

The safety system 80 is shown with reference to FIGS. 8–10 and essentially operates to automatically stop the input signal to the compression driver if the seal between the interface member 44 and the test panel is lost. During normal operation of the measurement system, the test panel will usually provide sufficient attenuation of the signal to prevent operator exposure to hazardous sound pressure levels. Referring to FIG. 8, the system 80 includes a harness 82 that is removably attached to the second end 45 of the waveguide tube 42. The harness 82 has a number of arms 84 that extend radially outward from the harness and in a slight forward direction (i.e., toward the test object during use). A push button switch 86 is mounted to the distal end of each arm. In FIGS. 8–10 there are three switches, one located on each of three arms. The switches 86 are wired in series (via lines 88) and are further in electrical communication with the power entering the amplifier 14. The switches are biased to an out position.

In the embodiment of FIGS. 8–10, the interface member is a flexible gasket 48. The arms 84 are positioned to result in the switches 86 being depressed when the gasket 48 is properly fit against the test object T. Likewise, if other interface members are used, such as the rigid flat annular adapter 50, the safety system 80 may be diametrically enlarged so that the switches are depressed directly by the test object T when the test head is properly positioned.

Therefore, when the safety system is properly positioned against a test object, all of the switches 86 will be pushed in. This closes the switch circuit and allows power to feed the amplifier. If any one of the switches becomes pushed out, then the switch circuit will become broken, indicating the test head 16 is no longer in proper contact with the test object T. The amplified signal is restored when the interface member is once more in proper contact with the object T and the safety system switches 86 are once again depressed.

Because the signal cut-off occurs at the amplifier and not directly at the signal source (the DSA), there is no immediate indication that any loss of the signal occurred. When using a Hewlett Packard HP35670A DSA, the pressures detected by the microphones are checked to ensure that the desired noise test level was achieved. If more than a certain amount of the microphone pressures measured are below the critical value for the test, the DSA assumes some loss of the signal occurred and repeats the measurement. After three attempts at measuring a particular sound pressure level, a warning is displayed on a screen informing the user that the measured sound level is insufficient for the test being conducted. Once the operator checks to ensure that everything has been hooked up properly and that the required seal has been achieved, the measurement for that level may be repeated.

As will be appreciated by those with skill in the art from a reading of the above, the present invention acoustic impedance system provides a unique, portable, nondestructive means of measuring various types of acoustic panels. By using different test heads, the system can easily accommodate various types, sizes, and shapes of test objects. The system is also capable of ensuring, that both microphones are properly calibrated and that workers will not be inadvertently exposed to high noise levels.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A portable acoustic impedance data acquisition and processing system for use with a test object, the system comprising:
   (a) a dynamic signal analyzer for providing audio output test signals;
   (b) a test head comprising:
      (i) a compression driver for providing an acoustic signal;
      (ii) a cylindrical waveguide tube with first and second ends, the first end connected to the compression driver and receiving the acoustic signal, the second end being open; the tube including a side opening near the tube second end;
   (c) a removable microphone holder attached to the waveguide tube at its side opening and two microphones insertable into the microphone holder; the microphones providing measured signals to the dynamic signal analyzer, the dynamic signal analyzer performing an acoustic analysis of the measured signals and making the results available to an operator;
   (d) a cylindrical endcap fitting, a mounting disc, and a plug for use in calibrating and adjusting microphone measurements; the endcap fitting including a first end adapted to engage the second end of the waveguide tube and a second end having an opening to hold the mounting disc, the mounting disc adapted to hold the microphones at a longitudinal orientation during calibration; the plug being positionable within the waveguide tube side opening during calibration to prevent the loss of a test signal;
   (e) an amplifier coupled to the dynamic signal analyzer for amplifying the audio output test signals and providing the amplified signal to the compression driver for use as the acoustic signal; and
   (f) at least one power supply for providing electrical power to the dynamic signal analyzer, the amplifier, and the two microphones.

2. The portable system according to claim 1, wherein the test head includes a flexible annular interface gasket adapted to attach to the waveguide tube second end.

3. The portable system according to claim 2, further comprising a safety system attached to the second end of the wave guide tube and in communication with at least one of the interface gasket and the test object, the system including a harness with at least two arms extending radially therefrom, each arm having a switch having a pushed in state and a pushed out state; wherein the switches are electrically linked in series and are connected to the amplifier and adapted to disrupt the amplifier from providing an amplified signal when any one of the switches is in a pushed out state.

4. The portable system according to claim 1, wherein the test head includes a rigid flat annular adapter attached to the wave guide tube second end and a flat compressible annular gasket attached to the adapter.

5. The portable system according to claim 1, wherein the test head includes a plug sample holder having a first end attached to engage the wave guide tube second end, an inner chamber adapted to hold a test sample, and a push plate located in the chamber to position the test sample near the holder first end.

6. The portable system according to claim 1, wherein the dynamic signal analyzer receives inputs of ambient temperature and ambient air pressure for use in performing acoustic analysis of the measured signals.

7. The portable system according to claim 1, wherein the first end of the cylindrical wave guide tube is removably connected to the compression driver via a removable mounting plate.

8. The portable system according to claim 1, wherein the dynamic signal analyzer saves the data results on an electronically-readable medium.

9. A portable acoustic impedance data acquisition and processing system for use with a test object, the system comprising:
   (a) a dynamic signal analyzer for providing audio output test signals;
   (b) a test head comprising:
      (i) a compression driver for providing an acoustic signal;
      (ii) a cylindrical waveguide tube with first and second ends, the first end connected to the compression driver and receiving the acoustic signal, the second end being open; the tube further including a side opening near the tube second end; and
   (c) a removable microphone holder attached to the waveguide tube side opening and two microphones insertable into the microphone holder; the microphones providing measured signals to the dynamic signal analyzer, the dynamic signal analyzer performing an acoustic analysis of the measured signals and making the results available to an operator;

(d) an amplifier coupled to the dynamic signal analyzer for amplifying the audio output test signals and providing the amplified signal to the compression driver for use as the acoustic signal; and (e) a safety system attached to the second end of the wave guide tube and in communication with at least one of the interface gasket and the test object, the system including a harness with at least two arms extending radially therefrom, each arm having a switch having a pushed in state and an pushed out state; wherein the switches are electrically linked in series and are connected to the amplifier and adapted to disrupt the amplifier from providing an amplified signal when any one of the switches is in an pushed out state; and (f) at least one power supply for providing electrical power to the dynamic signal analyzer, the amplifier, and the two microphones.

* * * * *